United States Patent
Iyer et al.

(10) Patent No.: US 9,351,688 B2
(45) Date of Patent: May 31, 2016

(54) LOW POWER MONITORING SYSTEMS AND METHOD

(71) Applicant: Covidien LP, Mansfield, MA (US)

(72) Inventors: Darshan Iyer, Superior, CO (US); Mark Su, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 682 days.

(21) Appl. No.: 13/753,046

(22) Filed: Jan. 29, 2013

(65) Prior Publication Data

US 2014/0214330 A1    Jul. 31, 2014

(51) Int. Cl.
*A61B 5/1455*   (2006.01)
*A61B 5/00*     (2006.01)

(52) U.S. Cl.
CPC .............. *A61B 5/7203* (2013.01); *A61B 5/002* (2013.01); *A61B 5/14551* (2013.01); *A61B 5/7221* (2013.01); *A61B 5/7278* (2013.01)

(58) Field of Classification Search
CPC ............. A61B 5/1455; A61B 5/14551; A61B 5/14552; A61B 5/00; A61B 5/0002; A61B 5/72; A61B 5/7235; A61B 5/7271; A61B 5/7278
See application file for complete search history.

(56) References Cited

U.S. PATENT DOCUMENTS

| | | |
|---|---|---|
| 5,351,685 A | 10/1994 | Potratz |
| 5,490,523 A | 2/1996 | Isaacson et al. |
| 5,533,507 A | 7/1996 | Potratz |
| 5,575,284 A | 11/1996 | Athan et al. |
| 5,577,500 A | 11/1996 | Potratz |
| 5,590,652 A | 1/1997 | Inai |
| 5,746,697 A | 5/1998 | Swedlow et al. |
| 5,792,052 A | 8/1998 | Isaacson et al. |
| 5,803,910 A | 9/1998 | Potratz |
| 5,924,979 A | 7/1999 | Swedlow et al. |
| 6,005,658 A | 12/1999 | Kaluza et al. |
| 6,011,985 A | 1/2000 | Athan et al. |
| 6,226,539 B1 | 5/2001 | Potratz |
| 6,496,711 B1 | 12/2002 | Athan et al. |
| 6,697,655 B2 | 2/2004 | Sueppel et al. |
| 6,697,658 B2 | 2/2004 | Al-Ali |
| 6,711,426 B2 | 3/2004 | Benaron et al. |

(Continued)

FOREIGN PATENT DOCUMENTS

| | | |
|---|---|---|
| EP | 734223 | 10/1996 |
| JP | 2237544 | 9/1990 |

(Continued)

OTHER PUBLICATIONS

International Search Report and Written Opinion for PCT Application No. PCT/US2014/013515 dated Apr. 24, 2014; 7 pgs.

(Continued)

*Primary Examiner* — Eric Winakur
(74) *Attorney, Agent, or Firm* — Fletcher Yoder PC (57) ABSTRACT

The present disclosure relates to systems and methods for collecting patient data via a monitoring system, with reduced power consumption. In one embodiment, the monitoring system is configured to emit pulses of light, and detect the light after passing through patient tissue. The light data is emitted sporadically, and a waveform is reconstructed from the sporadically sampled light data. Physiological parameters from the patient may be calculated from the reconstructed waveform. The sporadic sampling may reduce the power consumption by the monitoring system.

32 Claims, 9 Drawing Sheets

(56) References Cited

U.S. PATENT DOCUMENTS

| | | | |
|---|---|---|---|
| 6,731,967 | B1 | 5/2004 | Turcott |
| 6,863,652 | B2 | 3/2005 | Huang et al. |
| 6,912,413 | B2 | 6/2005 | Rantala et al. |
| 7,015,451 | B2 | 3/2006 | Dalke et al. |
| 7,162,288 | B2 | 1/2007 | Nordstrom et al. |
| 7,295,866 | B2 | 11/2007 | Al-Ali |
| 8,506,500 | B2 | 8/2013 | Li et al. |
| 2003/0195402 | A1 | 10/2003 | Fein et al. |
| 2005/0084202 | A1 | 4/2005 | Smith et al. |
| 2005/0234317 | A1 | 10/2005 | Kiani |
| 2006/0092029 | A1 | 5/2006 | Browne et al. |
| 2006/0275920 | A1 | 12/2006 | Petrilla et al. |
| 2007/0038049 | A1 | 2/2007 | Huang |
| 2007/0208240 | A1 | 9/2007 | Nordstrom et al. |
| 2007/0219453 | A1 | 9/2007 | Kremliovsky et al. |
| 2007/0282178 | A1 | 12/2007 | Scholler et al. |
| 2007/0282183 | A1 | 12/2007 | Scholler et al. |
| 2008/0015452 | A1 | 1/2008 | Ricci |
| 2008/0064936 | A1 | 3/2008 | Al-Ali |
| 2011/0294453 | A1* | 12/2011 | Mishali ............... H04B 1/0092 455/293 |
| 2012/0250748 | A1* | 10/2012 | Nguyen ............... G01S 13/90 375/224 |
| 2014/0046208 | A1* | 2/2014 | Sejdic ............... A61B 5/7232 600/300 |

FOREIGN PATENT DOCUMENTS

| | | |
|---|---|---|
| JP | 3939782 | 7/2007 |
| RU | 2294141 C1 | 2/2007 |
| WO | WO2006080856 | 8/2006 |
| WO | WO2006083180 | 8/2006 |

OTHER PUBLICATIONS

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Such, Hans Olaf; "Optoelectronic Non-invasive Vascular Diagnostics Using multiple Wavelength and Imaging Approach," *Dissertation*, (1998).

Odagiri, Y.; "Pulse Wave Measuring Device," *Micromechatronics*, vol. 42, No. 3, pp. 6-11 (published Sep. 1998) (Article in Japanese—contains English summary of article).

Shamir, M., et al.; "Pulse oximetry plethysmographic waveform during changes in blood volume," British Journal of Anaesthesia 82(2): 178-81 (1999).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Kaestle, S.; "Determining Artefact Sensitivity of New Pulse Oximeters in Laboratory Using Signals Obtained from Patient," *Biomedizinische Technik*, vol. 45 (2000).

Hamilton, Patrick S., et al.; "Effect of Adaptive Motion-Artifact Reduction on QRS Detection," *Biomedical Instrumentation & Technology*, pp. 197-202 (May-Jun. 2000).

Kim, J.M., et al.; "Signal Processing Using Fourier & Wavelet Transform for pulse oximetry," pp. II-310-II-311 (2001).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Huang, J., et al.; "Low Power Motion Tolerant Pulse Oximetry," Anesthesia & Analgesia 2002 94: S103.

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Johansson, A.; "Neural network for photoplethysmographic respiratory rate monitoring," *Medical & Biological Engineering & Computing*, vol. 41, pp. 242-248 (2003).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Wu, Dongmei, et al.; "Na*/H* Exchange inhibition delays the onset of hypovolemic circulatory shock in pigs," SHOCK, vol. 29, No. 4, pp. 519-525 (2008).

Chen, Liangyou, et al.; "IS respiration-induced variation in the photoplethysmogram associated with major hypovolemia in patients with actue tramatic injuries," SHOCK, vol. 34, No. 5, pp. 455-460 (2010).

McGrath, S.P., et al.; "Pulse oximeter plethysmographic waveform changes in awake, spontaneously breathing, hypovolemic volunteers," Anesth. Analg. vol. 112 No. 2, pp. 368-74 (2010).

U.S. Appl. No. 13/753,007, filed Jan. 29, 2013, Mark Su.

* cited by examiner

LOW POWER MONITORING SYSTEMS AND METHOD

BACKGROUND

The present disclosure relates generally to medical sensors and, more particularly, to low power medical sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor and sense certain physiological characteristics of their patients. Accordingly, a wide variety of devices has been developed for monitoring and sensing many such physiological characteristics. For example, one category of monitoring and sensing devices includes spectrophotometric monitors and sensors. This category of device studies the electromagnetic spectra (e.g., wavelengths of light) and can monitor a suite of physiological parameters. Such devices provide doctors and other healthcare personnel with the information they need to provide quality healthcare for their patients. As a result, such monitoring and sensing devices have become an indispensable part of modern medicine.

Conventional spectrophotometric sensors are typically connected to a monitor via a cable. The cable provides the sensor with power and acts as a conduit for the transmission of signals between the sensor and the monitor. However, the cable also acts to tether the patient to the monitor, preventing unencumbered motion by the patient. As a result, such cable-based systems may not be suitable for ambulatory patients or for applications that require remote monitoring in non-clinical environments. Accordingly, various systems have been proposed which include a patient sensing device connected to a local monitor by way of a wireless link. Unfortunately, sensors that incorporate a wireless link may be limited to power provided on the sensor itself, which may be drained very quickly.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to systems, methods, and devices for improving power consumption and lifespan of wireless medical sensors. Present embodiments may apply to a variety of wireless medical sensors, including sensors for measuring a photoplethysmograph (PPG), patient temperature, transvascular fluid exchange volumes, tissue hydration, blood flow, blood microcirculation, respiration, blood pressure, ECG (electrocardiography), pulse transit time, and/or others. For example, in one embodiment, a medical sensor system may include a medical sensor and a patient monitor that communicate with each other via wireless transmission circuitry. The sensor sporadically emits pulses of light (e.g., randomly, pseudo-randomly, or at predetermined irregular intervals) into a patient's tissue, in response to light drive signals. A detector, which may also be located on the sensor, detects the light attenuated by the patient's tissue, and collects data samples corresponding to the detected sporadic light pulses. Either the sensor or monitor may process the data samples to estimate physiological parameters and/or to generate a PPG. The present disclosure provides systems and method for decreasing the amount of power used in collecting such data and measurements by configuring the sensor device to emit sporadic pulses of light rather than regular, frequent emission of light. This may reduce the amount of time that the sensor device spends in sensing the patient. The sensor device may expend less power and, accordingly, may have a longer battery life and overall lifespan.

Figure 1:
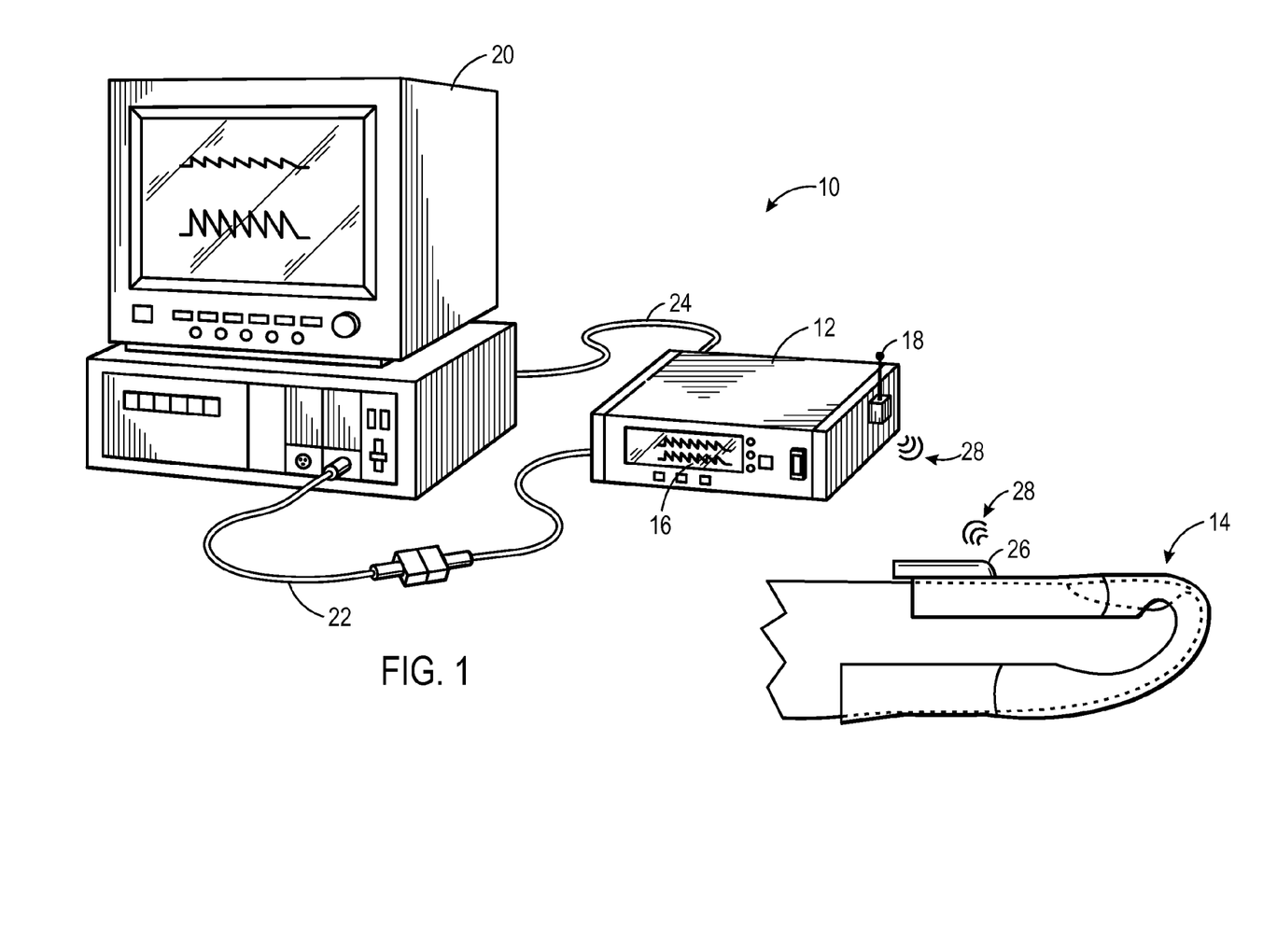
FIG. 1 illustrates components of a wireless medical sensor system, in accordance with one embodiment of the present disclosure.

With the foregoing in mind, FIG. 1 depicts an embodiment of a wireless medical sensor system 10 that may efficiently sense physiological characteristics of a patient with sporadic light pulses, thereby conserving power. Although the embodiment of the system 10 illustrated in FIG. 1 relates to wireless photoplethysmography, the system 10 may be configured to obtain a variety of medical measurements with a suitable medical sensor. For example, the system 10 may, additionally or alternatively, be configured to measure patient temperature, transvascular fluid exchange volumes, tissue hydration, blood flow, blood microcirculation, respiration, ECG, non-invasive blood pressures (NIBP), blood pulse transit time, and/or others. In the illustrated embodiment, the system 10 includes a patient monitor 12 that communicates wirelessly with a sensor 14. In certain embodiments, the patient monitor 12 and the sensor 14 may communicate over a wired connection, such as through a cable connecting the sensor 14 to the monitor 12. The application of embodiments herein to reduce power consumption by the sensor may be useful for both wired and wireless systems.

The patient monitor 12 may include a display 16, a wireless module 18 for transmitting and receiving wireless data, a memory, a processor, and various monitoring and control features. Based on data received from the wireless sensor 14, the patient monitor 12 may display patient measurements and perform various measurement or processing algorithms. For example, when the system 10 is configured for pulse oximetry, the patient monitor 12 may perform blood oxygen saturation calculations, pulse measurements, and other measurements based on the data received from the wireless sensor 14. Furthermore, to provide additional functions, the patient monitor 12 may be coupled to a multi-parameter patient monitor 20, for example via wireless communication and/or via a cable 22 connected to a sensor input port or via a cable 24 connected to a digital communication port. The multi-parameter patient module 20 may process and/or display physiological parameters from other sensors in addition to the data from the monitor 12 and sensor 14.

Like the patient monitor 12, the sensor 14 may include a wireless module 26. The wireless module 26 of the wireless sensor 14 may establish a wireless communication 28 with the wireless module 18 of the patient monitor 12 using any suitable protocol. By way of example, the wireless module 26 may be capable of communicating using the IEEE 802.15.4 standard, and may communicate, for example, using ZigBee, WirelessHART, or MiWi protocols. Additionally or alternatively, the wireless module 26 may be capable of communicating using the Bluetooth standard or one or more of the IEEE 802.11 standards. In an embodiment, the wireless module 26 includes a transmitter (such as an antenna) for transmitting wireless data, and the wireless module 18 includes a receiver (such as an antenna) for receiving wireless data. In an embodiment, the wireless module 26 also includes a receiver for receiving instructions (such as instructions to switch modes), and the wireless module 18 also includes a transmitter for sending instructions to the sensor.

Figure 2:
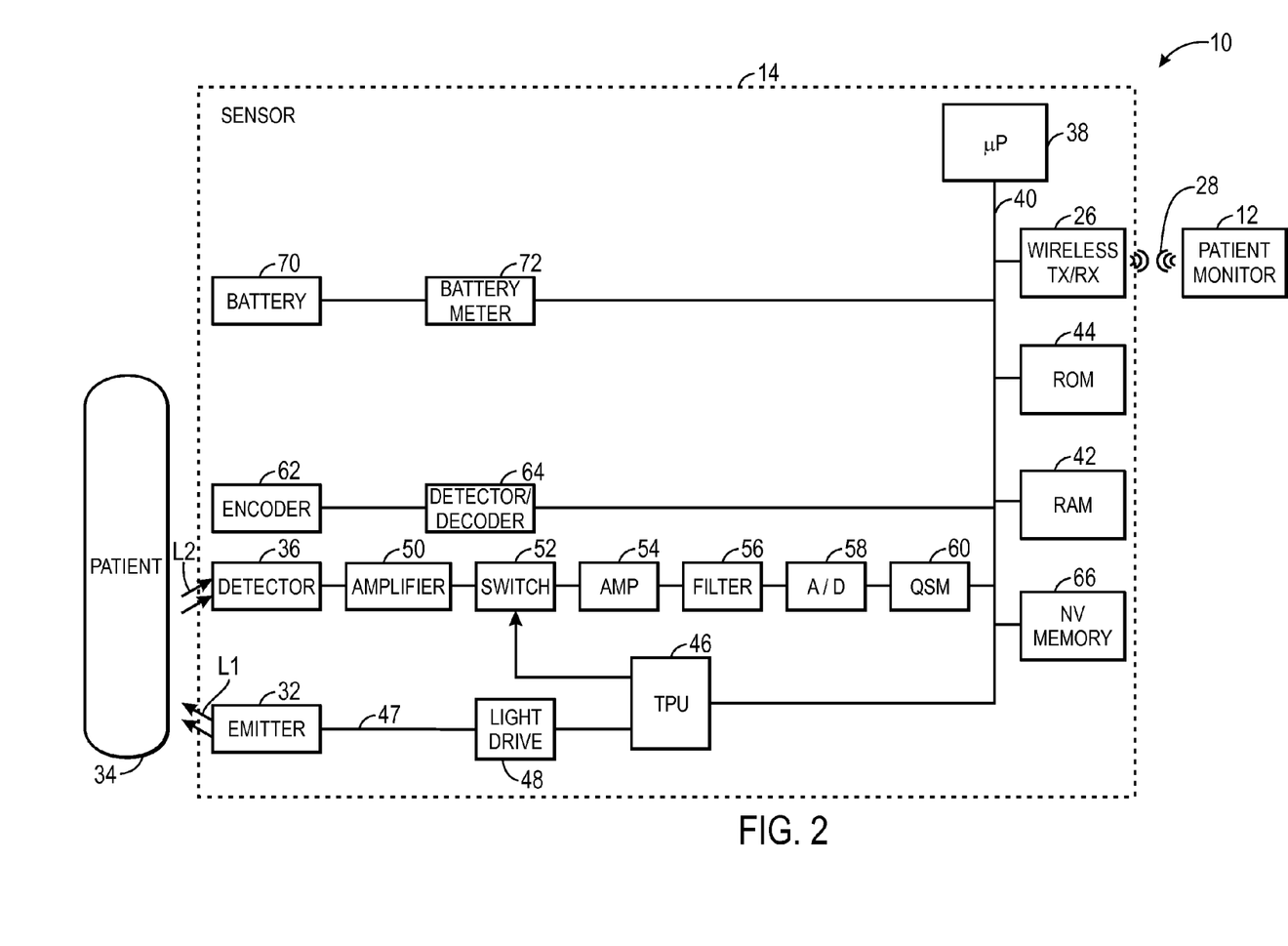
FIG. 2 depicts a schematic diagram of the system of FIG. 1, in accordance with one embodiment of the present disclosure.

FIG. 2 is a block diagram of an embodiment of the wireless medical sensor system 10 that may be configured to implement the techniques described herein. By way of example, embodiments of the system 10 may be implemented with any suitable medical sensor and patient monitor, such as those available from Covidien LP (Boulder, Colo.). The system 10 may include the patient monitor 12 and the sensor 14, which may be configured to obtain, for example, a plethysmographic signal from patient tissue at certain wavelengths. The sensor 14 may be communicatively connected to the patient monitor 12 via wireless communication 28. When the system 10 is operating, light L1 from an emitter 32 (e.g., light at certain wavelength(s)) may pass into a patient 34 where the portions of the light may be differentially scattered, absorbed, and/or transmitted. Light L2 that emerges from the patient tissue may detected by a detector 36. For example, the system 10 may emit light L1 from two or more LEDs or other suitable light sources into a pulsatile tissue. The reflected or attenuated light L2 may be detected with the detector 36, such as a photodiode or photo-detector, after the light has passed through or has been reflected by the pulsatile tissue. In certain embodiments, the emitter 32 may be configured to emit pulses of light at random, pseudo-random, or preset irregular intervals.

The sensor 14 may include a microprocessor 38 connected to an internal bus 40. Also connected to the bus 40 may be a RAM memory 42 and a ROM memory 44. A time processing unit (TPU) 46 may provide timing control signals to a light drive circuitry 48 which may control when the emitter 32 is illuminated, and if multiple wavelengths are emitted, the multiplexed timing for the different wavelengths. The TPU 46 may also control the gating-in of signals from the detector 36 through an amplifier 50 and a switching circuit 52. These signals may be sampled at the proper time, depending upon which of multiple wavelengths of light is emitted, if multiple wavelengths are used. In one embodiment, the received signal from the detector 36 may be passed through an amplifier 54, a low pass filter 56, and/or an analog-to-digital converter 58.

The digital data may then be stored in a queued serial module (QSM) 60, for later downloading to the RAM 42 as the QSM 60 fills up. In one embodiment, there may be multiple parallel paths of separate amplifier, filter and/or A/D converters for multiple light wavelengths or spectra received. This raw digital data may be further processed by the circuitry of the wireless medical sensor 14 into specific data of interest, such as pulse rate (heart rate), blood oxygen saturation, and so forth. Alternatively, the raw digital data may be transmitted to the patient monitor 12, where it may be further processed into specific data of interest.

In an embodiment, the sensor 14 may also contain an encoder 62 that encodes information indicating the wavelength of one or more light sources of the emitter 32, which may allow for selection of appropriate calibration coefficients for calculating a physiological parameter such as blood oxygen saturation. The encoder 62 may, for instance, be a coded resistor, EEPROM or other coding devices (such as a capacitor, inductor, PROM, RFID, parallel resonant circuits, or a colorimetric indicator) that may provide a signal to the processor 38 related to the characteristics of the sensor 14 that may allow the processor 38 to determine the appropriate calibration characteristics for the PPG components of the sensor 14. Further, the encoder 62 may include encryption coding that prevents a disposable or replaceable part of the sensor 14 from being recognized without corresponding adjustment or replacement of the information encoded by the encoder 62. In some embodiments, the encoder 62 and/or the detector/decoder 64 may not be present. Additionally or alternatively, the processor 38 may encode processed sensor data before transmission of the data to the patient monitor 12.

Figure 3:
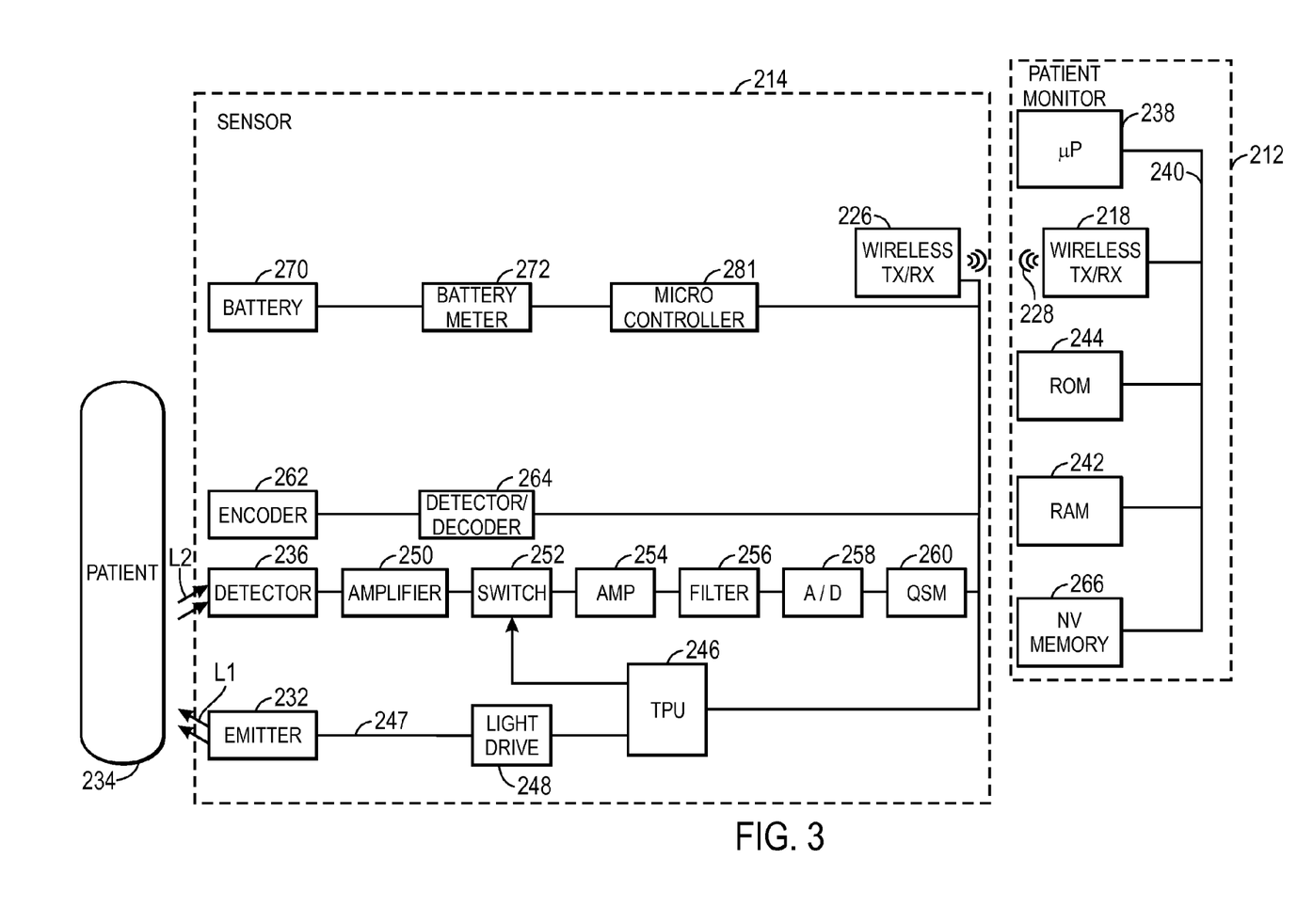
FIG. 3 depicts a schematic diagram of the system of FIG. 1, in accordance with one embodiment of the present disclosure.

It should be noted that the patient monitor 12 may include the components described above for the sensor 14 with a few exceptions (e.g., emitter 32 and detector 36) to implement the techniques described herein. A wireless medical sensor system 210 including a sensor 214 and patient monitor 212 according to another embodiment is shown in FIG. 3. As shown in FIG. 3, the microprocessor 238, ROM 244, RAM 242, and non-volatile Memory 266 are located on the patient monitor 212. In this case, the calculation of the physiological parameter by the processor 238 is accomplished on the monitor 212, rather than on the sensor 214. The sensor 214 operates similarly to that described above, by emitting light pulses into patient tissue, and detecting the reflected and/or scattered light. This raw light data is then passed to the microprocessor 238 on the monitor for further processing. The sensor 214 may also include a microcontroller 281, which controls the other components on the sensor.

Locating the microprocessor 238 and memory components 244, 242, 266 on the monitor 212 may reduce the power consumption and size of the wireless sensor 214. The sensor 214 acquires light data via the emitter 232 and detector 236, and transmits raw light data to the monitor 212 via wireless communication 228 (through wireless modules 226, 218). The monitor 212 then processes the raw data to calculate the physiological parameter(s), as described in further detail below.

In an embodiment, the sensor 214 may transmit the acquired signal data to another type of device, in addition to or instead of the monitor 212. The other device may be, for example, a smart phone, a laptop computer, a remote computer, a handheld computing device, or a cloud computing device. In an embodiment, the sensor 214 transmits data to a wireless network, which may process and/or store the data via various networked processors or memory devices.

In various embodiments, based at least in part upon the value of the received signals corresponding to the light L2 received by detector 36, the microprocessor 38 (or the processor 238 on the monitor 212) may calculate a physiological parameter of interest using various algorithms. For example, the microprocessor 38 may utilize algorithms (e.g., analog-to-information sensing algorithm) to estimate a physiological parameter, morphological features, and/or a PPG from sampled data acquired from the detected pulses of light. These algorithms may utilize coefficients, which may be empirically determined, corresponding to, for example, the wavelengths of light used. These may be stored in the ROM 44 or non-volatile memory 66. In a two-wavelength system, the particular set of coefficients chosen for any pair of wavelength spectra may be determined by the value indicated by the encoder 62 corresponding to a particular light source of the emitter 32. For example, the first wavelength may be a wavelength that is highly sensitive to small quantities of deoxyhemoglobin in blood, and the second wavelength may be a complimentary wavelength. Specifically, for example, such wavelengths may be produced by orange, red, infrared, green, and/or yellow LEDs. Each wavelength may be associated with a different coefficient stored in the encoder 62. Different wavelengths may be selected based on instructions or protocols received from the patient monitor 12, based on preferences stored in a nonvolatile storage 66, or based on user input. User input may be inputted at the monitor 12, such as by a user interface provided on the monitor, and/or may be inputted to a remote host computer, which communicates with the monitor 12 via a suitable port or communication link. The instructions from the patient monitor 12 may be transmitted wirelessly to the sensor 14.

The nonvolatile memory 66 may store caregiver preferences, patient information, or various parameters, discussed below, which may be used in the operation of the sensor 14. Software for performing the configuration of the sensor 14 and for carrying out the techniques described herein may also be stored on the nonvolatile memory 66 and/or on the ROM 44. The nonvolatile memory 66 and/or RAM 42 may also store historical values of various discrete medical data points. By way of example, the nonvolatile memory 66 and/or RAM 42 may store the past or last known values for one or more physiological parameters such as oxygen saturation, pulse rate, respiratory rate, respiratory effort, blood pressure, vascular resistance, and/or vascular compliance. In an embodiment, the nonvolatile memory 66 and/or RAM 42 store the raw data points corresponding to the light L2 detected by the detector.

A battery 70 may supply the sensor 14 with operating power. By way of example, the battery 70 may be a rechargeable battery, such as a lithium ion or lithium polymer battery, or may be a single-use battery such as an alkaline or lithium battery. Due to the techniques described herein to reduce battery consumption, the battery 70 may be of a lower capacity, and accordingly smaller and/or cheaper, than a battery needed to power a similar sensor 14 that does not employ these techniques. A battery meter 72 may provide the expected remaining power of the battery 70 to a user and/or to the microprocessor 38.

The system 10 may be configured to sporadically emit pulses of light from the sensor 14 onto the patient at random, pseudo-random, or predetermined irregular (i.e., non-uniform) intervals, such that the emitter 32 is energized for a smaller amount of time than it would be conventionally. For example, pulses may be emitted at an average frequency in the range of every 100 to 700 milliseconds (ms), with a LED pulse length in the range of 10 to 50 ms. The average frequency is an average of the irregular intervals at which the pulses are emitted. As such, data collected by the detector 36 may be a set of sporadic data samples rather than a full dataset (e.g., data gathered via frequent, regular emission of light for an extended length of time).

The light drive 48, 248 emits a light drive signal that instructs the emitter 32, 232 when to emit light. In an embodiment, the light drive signal includes a predetermined set of random, pseudo-random or irregular intervals at which the emitter emits light. The light drive signal may include two such sets of irregular intervals, one for activating the red LED and a different one for activating the infrared LED, or the two LED's may be activated according to the same set of irregular intervals. The light drive signal may also be used to power the detector amplifier 50, 250 and/or ADC 58, 258 on and off, such that the amplifier and/or ADC is turned off between light pulses, to conserve power. Alternately, the detector and associated components may be left on continuously, to detect the light pulses L2 from the patient tissue any time they arrive at the detector.

The system 10 may use the sporadic data samples to estimate one or more physiological parameters of the patient, morphological parameters of the data samples, and/or a PPG. These physiological parameters may include pulse rate, respiration rate, respiratory effort, blood pressure, vascular resistance, vascular compliance, oxygen saturation, and/or others. In some embodiments, these processes or acts may be done by a processor executing code in the sensor 14 or in the patient monitor 12.

In estimating a physiological parameter, signal probability distribution may be estimated using the currently collected sporadic data samples (e.g., from detection of light L2, see FIG. 2, at one or more wavelengths such as red and infrared). Additionally, a prior probability obtained from the last known measurement or value of the physiological parameter of the patient may be used along with the estimated probability distribution of the current set of data samples to obtain a Bayesian probability function for the physiological parameter. The maximum likelihood frequency function may be applied to the sporadic data samples to reconstruct a waveform representative of a PPG that fits the data samples. An embodiment of this process is illustrated in further detail below.

Figure 4:
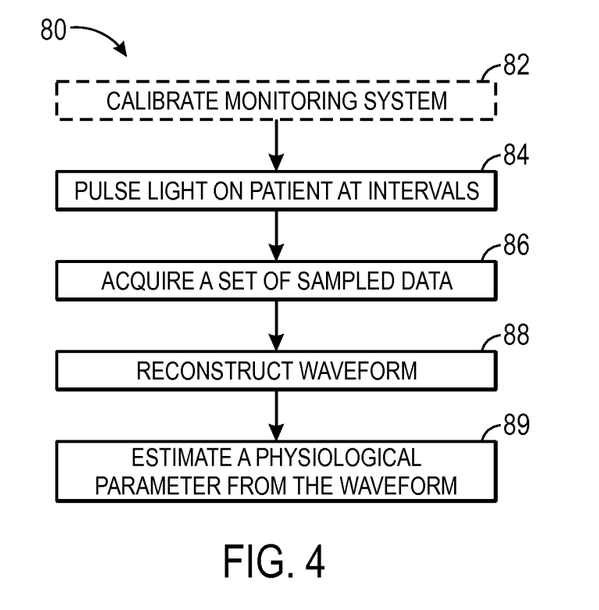
FIG. 4 depicts a flow diagram of a method for obtaining a physiological parameter from a patient, in accordance with an embodiment of the present disclosure.

FIG. 4 illustrates a process 80 for obtaining a physiological parameter of the patient with the system 10, according to an embodiment of the present disclosure. In certain embodiments, the system 10 may first be calibrated (82) for the patient, as the system 10 may operate differently for different patients or in different scenarios. However, in some embodiments, the system 10 may not be calibrated and thus, the calibration step (82) may be omitted. During the process, the system 10 may pulse (84) light on the patient via the emitter 32 of the sensor 14 at random, pseudo-random, or preset irregular intervals, for a stipulated duration. The emitter 32 may generally use power during the pulses and not use power or use very little power before, after, and/or in between the pulses. This reduces the power consumed by the emitter 32 during the process 80. The system 10 may then acquire (86) a set of sampled data representative of the detected pulses of light. This may be done by the detector 36 of the sensor 14. The system 10 may then reconstruct a PPG waveform (88) based on the data samples. The system 10 may then estimate (89) a physiological parameter from the reconstructed waveform. In certain embodiments, the system 10 may estimate more than one physiological parameter. The calibration (82) and the reconstruction (88) will be shown in further detail in FIGS. 5 and 7, respectively.

Figure 5:
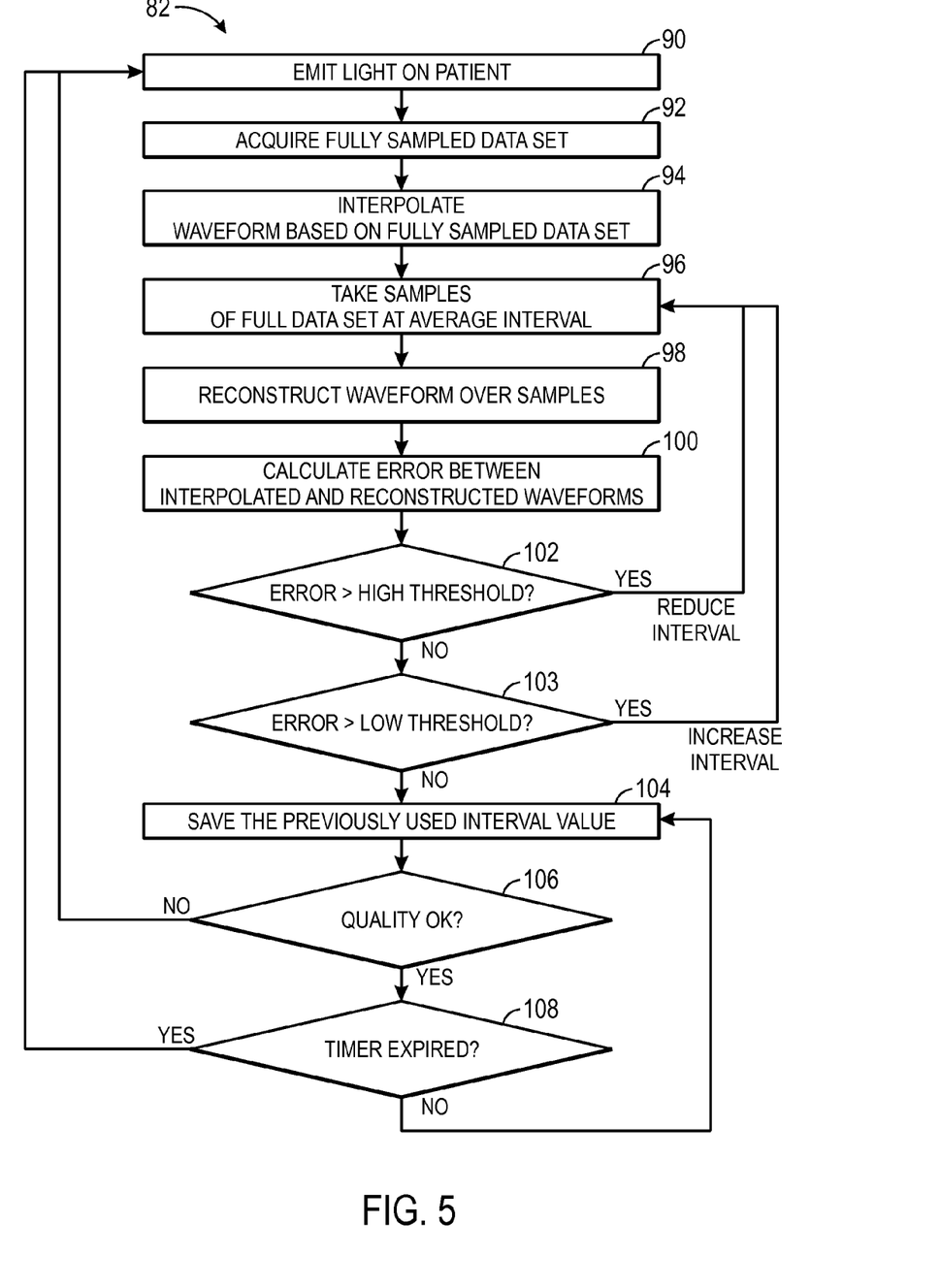
FIG. 5 depicts a flow diagram of a method for adjusting an average sampling interval, in accordance with an embodiment of the present disclosure.

As mentioned, in certain embodiments, the system 10 may be calibrated (82). Different patients may exhibit physiological parameters with varying degrees of stability. As such, the sampling frequency and duration to be used in pulsing light may be adjusted accordingly. For example, a patient with relatively stable physiological parameters may be subject to a lower sampling rate or duration as the sampled data may have a higher degree of accuracy. Conversely, a patient with relatively unstable physiological parameters may benefit from a higher sampling rate or duration in order to obtain sampled data with a sufficient degree of accuracy. Calibration may also be useful to account for variations in signal strength, patient perfusion, ambient noise, interference, and other factors. FIG. 5 illustrates the calibration process 82. During calibration, the system 10 may emit light (90) on to the patient (e.g., pulsatile tissue of the patient) for whom the system 10 is being calibrated.

To calibrate the system, the system first acquires a fully sampled dataset (92) over a period of time. The fully sampled dataset is obtained by emitting light (90) at regular intervals at a relatively high frequency, as compared to the sporadic pulses emitted at an overall lower average frequency during low power operation. During this period of time, the emitter 32 emits light in regular pulses to acquire a fully sampled dataset (92) rather than a sporadically sampled dataset. The fully sampled dataset may generally represent a complete measurement of the patient status (e.g., multiple physiological parameters), and may generally reflect the patient status with a high degree of accuracy. The system 10 may then interpolate (94) the data to form a waveform, such as a PPG waveform, from the fully sampled dataset. Optionally, the calibration may also include calculating a physiological parameter from the waveform. Typically, physiological parameters obtained from the interpolated waveform of the fully sampled dataset have a high degree of accuracy.

After obtaining a waveform from the fully sampled dataset (94), the system 10 then takes (96) a subset of sporadic samples from the fully sampled dataset at a first average sampling interval. The result is a sub-set of sporadic data samples. Although the interval between samples varies in this sporadic data subset, the overall subset has an average sampling interval (e.g., average time between sampling, over the duration of the sampling), which is longer than the average sampling interval of the fully sampled dataset (i.e., the average frequency of the sporadic data sub-set is lower than the frequency of the fully sampled dataset). This sub-sampling from the full dataset may simulate a condition in which the system 10 is operating on a patient by pulsing light at irregular intervals and collecting the corresponding sampled data.

After taking the sporadic samples from the full dataset, the system 10 may reconstruct a waveform from the data subset (98) (as discussed in more detail below). The reconstructed waveform may then be compared (100) to the interpolated waveform from the full dataset (at 94) to calculate an error between the two waveforms. The process 82 may then include determining if the error is below an upper error threshold (102). If the error between the two waveforms is equal to or above the upper error threshold, then the process returns to take another subset of samples of the full dataset with a reduced average sampling interval. That is, the average sampling interval is reduced such that more samples are taken. The process is then repeated to reconstruct a waveform from the new data subset, and compare this value to the waveform from the full dataset, and the process may continue until the error between the waveforms falls below the upper error threshold.

Optionally, the process may also include determining whether the error between the waveforms falls below a lower threshold (103). This step ascertains whether the reconstructed waveform from the data subset is too close to the interpolated waveform from the full dataset. This may indicate that the average sampling interval is shorter (frequency is higher) than it needs to be, and that a longer interval between sampling may be used to save power. If the error is below the lower threshold, then the process increases the average sampling interval and returns to take another set of samples from the full dataset (96). In other words, the system may operate with an upper and lower threshold, and may calibrate via process 82 until the error threshold is between the upper and lower allowable amounts.

If the error between the two waveforms is between the upper and lower thresholds (or below an upper threshold, where a lower threshold is not used), then the system continues reconstructive sensing (104) at the average sampling interval that was just obtained by the calibration process. The system may save the average interval value that was used to obtain the subset of samples (at 96) and use this for operation of the sensor on a patient. When the error is within the established threshold(s), the average sampling interval is sufficient to obtain the desired waveform, and the emitter may be configured to pulse light at such a rate. The calibration process works to balance the competing demands of high fidelity and low power consumption.

The method may also include evaluating the quality of the reconstructed waveform during ongoing reconstructive sensing (106). The system may use various signal quality metrics to evaluate the reconstructed waveform and determine if the waveform meets the minimum signal quality requirements. If the reconstructed waveform does not meet the quality requirements, then the process returns to emit light on the patient (90) and acquire a new full dataset (92).

The system may be programmed to periodically repeat the calibration process (82) to re-assess the average sampling interval and determine if it should be changed given the existing patient and environmental conditions. In one embodiment, the method includes using a timer to trigger the calibration. After establishing an average sampling interval, the system continues reconstructive sensing (104) until either the signal quality decreases (106) or a timer expires (108). If the timer is expired, the process returns to emit light on the patient (90) and acquire a new full dataset (92).

In place of or in addition to comparing the two waveforms, the calibration may include calculating a physiological parameter from each waveform, and comparing the two calculated physiological parameters. The process includes calculating the difference between the physiological parameter calculated from the reconstructed waveform from the sampled data subset and the physiological parameter calculated from the interpolated waveform from the fully sampled dataset. If this difference is within an error threshold, the average sampling interval may be saved for use in operation on the patient. If not, the average sampling interval may be reduced or increased and the process repeated.

As mentioned, in one embodiment the system 10 is generally configured to perform reconstructive sensing to reduce the power consumed by the sensor for light pulses and sampling. The system is configured to pulse light sporadically (that is, at irregular, random, pseudo-random, or non-uniform intervals) on the patient in order to collect a set of sampled data (sporadically sampled data) representative of the patient status. The system 10 may then reconstruct a waveform, such as a PPG waveform, from the sampled data, and estimate one or more physiological parameters from the reconstructed waveform.

Figure 6:
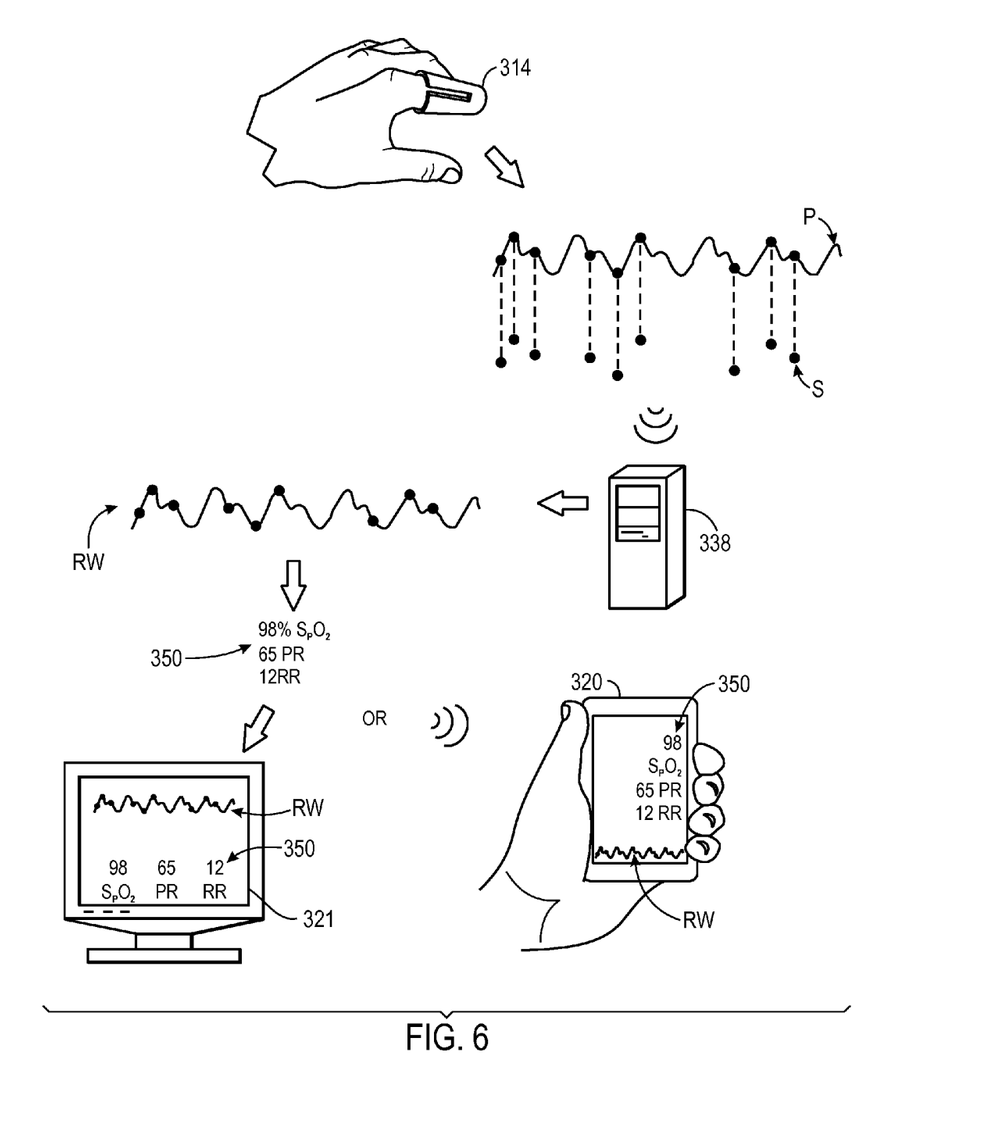
FIG. 6 depicts a system for reconstructive sensing, in accordance with an embodiment of the present disclosure.

A reconstructive sensing system is shown in FIG. 6. The system includes a wireless sensor 314 which detects the underlying physiological signal P. The sensor acquires sporadic samples S from the signal P. The wireless sensor transmits these samples wirelessly to a processor 338. The processor receives the sporadic data samples and creates a reconstructed waveform RW which fits the samples S. The processor is powered by a power supply such as an AC wall outlet. The processor may then calculate physiological parameters 350 from the reconstructed waveform RW, and transmit the parameters and/or the reconstructed waveform to a display such as a handheld unit 320 or a monitor 321.

In an embodiment, reconstructive sensing is accomplished to reconstruct a waveform from the sporadic data samples by creating a weighted sum of functions stored in a dictionary of functions. The individual functions in the dictionary may also be referred to as atoms. These individual functions in the dictionary may include wavelets, sinusoids, or other functions. Examples include Gabor atoms, wavelet functions, sine waves, etc.

In one embodiment, the dictionary may include portions of synthetic or real waveforms obtained from patients, such as synthetic or real PPG waveforms. The dictionary may include waveforms that correspond with different patient and/or environmental conditions, and the system may be programmed to access the relevant portions of the dictionary given the current conditions in operation on a particular patient.

The dictionary can be created or adjusted depending on the type of waveform being sampled and the known characteristics of that type of waveform. For example, when the waveform being sampled is a PPG waveform from a pulse oximeter, the waveform is expected to behave similar to a repeating sinusoid, within an expected range of amplitude and frequency. Suitable dictionary components are chosen for the dictionary based on this information. The dictionary may be customized for the desired physiological parameter, and/or for the particular patient and/or environmental conditions. The customized dictionary along with the sporadic samples of the particular waveform being sampled enable the waveform to be reconstructed from the samples.

Figure 7:
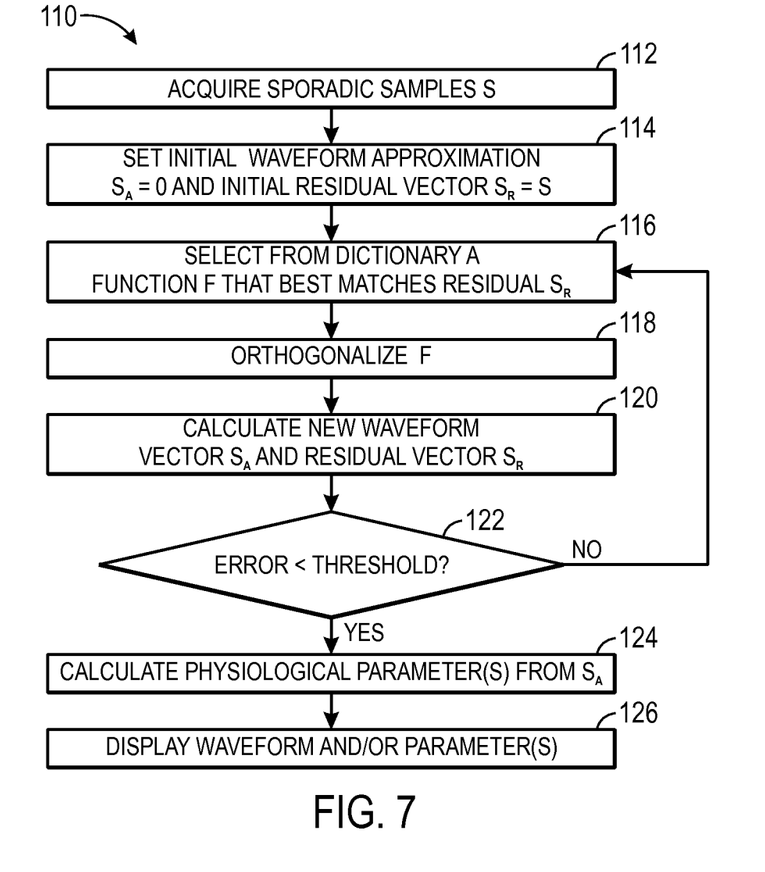
FIG. 7 depicts a flow diagram of a method for obtaining an estimated physiological parameter from the wireless medical system of FIG. 1, in accordance with an embodiment of the present disclosure.

A method for reconstructive sensing (110) according to an embodiment of the disclosure is illustrated in FIG. 7. A set of sporadic samples S from the light detector 36, 236 of the sensor 14, 214 is used to reconstruct a waveform in the following steps. Given a sporadically sampled signal S and a dictionary of elements $v_1, \ldots, v_n$, initialize by setting the current approximation of the waveform $S_A=0$ and the current residual $S_R=S$ (114). The process then proceeds iteratively, until a number of iterations equals a maximum number, or until the error between the samples S and the reconstructed waveform is less than a threshold (as discussed further below). In each iteration, the process includes choosing a dictionary element to approximate the residual $S_R$ (116). In an embodiment, this can be done by selecting a function F from the dictionary that best matches the residual vector $S_R$. In an embodiment, the function F that best matches the residual vector $S_R$ is the function that maximizes the dot product between the function and the residual.

Once a dictionary element F is chosen, the process may include orthogonalizing the dictionary element F (118). This is done by forming a linear combination of the previously chosen dictionary elements and orthogonalizing the currently chosen dictionary element F by subtracting this linear combination from the currently chosen dictionary element F. This step is taken so that none of the previously chosen elements is reintroduced, and thus the updated function does not contain redundancy. The process then includes updating the current approximation of the waveform $S_A$ and the residual $S_R$ (120). In an embodiment, this is accomplished as follows:

$$S_{Anew} = S_A + \left(\frac{F}{\|F\|} \circ S_R\right) \circ \frac{F}{\|F\|} \quad (1)$$

and $$S_{Rnew} = S_R - \left(\frac{F}{\|F\|} \circ S_R\right) \circ \frac{F}{\|F\|} \quad (2)$$

The waveform $S_A$ is the sum of the selected dictionary elements. The above process may be referred to as orthogonal matching pursuit. It should be noted that the step of orthogonalizing the selected function is optional, and the process may be implemented without this step, in which case the process may be referred to simply as matching pursuit.

Once the error between the sporadic set of samples S and the approximation waveform $S_A$ falls below a threshold or the algorithm runs out of maximum number of iterations, the approximation waveform $S_A$, calculated from a set of the sporadically sampled waveform, represents the fully sampled, densely represented waveform. Thus, a waveform can be obtained without fully sampling data from the patient, thereby reducing the amount of power needed to operate the emitter and other components on the sensor 14, 214. In one embodiment, the error may fall below the threshold after only 5 iterations, selecting 5 functions from the dictionary. In other embodiments, the number of selected functions may range from about 3-10 functions.

The method then includes calculating physiological parameters from the reconstructed waveform (124). Any suitable algorithm or process for calculating parameters from a waveform may be used. In an embodiment, an algorithm used to calculate parameters from a fully sampled waveform may also be used for calculating parameters from the reconstructed waveform. The reconstructed waveform is provided as an input to such algorithms just as the fully sampled waveform may be. In this way, the algorithm used to calculate the physiological parameter need not be changed depending on whether the waveform is fully sampled or reconstructed, and wireless sensors utilizing reconstructive sensing may be integrated into systems with existing algorithms for calculating physiological parameters from waveforms. Various physiological parameters may be calculated, such as respiratory rate, pulse rate, respiratory effort, blood pressure, carbon dioxide levels, oxygen saturation, vascular resistance, vascular compliance, carbon monoxide level, stroke volume, and/or others. In one embodiment, the oxygen saturation for the patient is calculated based on a ratio-of-ratios calculation from the reconstructed waveform, where each ratio is calculated from a reconstructed waveform of red or infrared wavelength. In an embodiment, physiological parameters may be calculated directly from the selected dictionary elements $F_i$, before the waveform is reconstructed. For example, if the waveform is a PPG, electrocardiogram (ECG), or arterial pressure waveform, the frequency of the best atom selected by matching pursuit may represent the heart rate or respiratory rate of the patient, without the need for further processing.

The method may also include displaying the parameter(s) and/or the reconstructed waveform on a display (126). The display may be attached to a processor, or may be remotely located, such as on a tablet, smartphone, or wristwatch display.

The waveform reconstruction may be performed by any suitable processor, such as the processor 38 or 238. In one embodiment, the reconstruction is not performed on the sensor 14, 214. The sensor 14, 214 sends the raw sporadic data samples S to another processor, which performs the reconstruction. For example, the sensor may send the raw data to the processor 238 on the monitor 210. In this manner, the sensor itself does not consume power to perform the reconstruction. The reconstruction may be performed by a processor that has access to a more robust power supply than the sensor, such as a large battery or an AC power source. In an embodiment, the processing set forth in FIG. 7 at 114 through 124 may be performed by the processor 38 or 238.

In an embodiment, the waveform being sampled is a PPG waveform from a pulse oximeter. The pulse oximeter obtains sporadic samples of detected light from two different wavelengths, such as red and infrared. The matching pursuit method may be used separately for both the red and infrared sample sets, creating two reconstructed light waveforms. Blood oxygen saturation can then be calculated from the reconstructed waveforms, using a known ratio-of-ratios calculation. In other embodiments, other waveforms may be sampled and reconstructed to calculate other physiological parameters. Examples include ECG (electrocardiogram), PPG, arterial pressure, EEG, capnography, and others.

The process outlined in FIG. 7 utilizes sporadic data sampling to generate a waveform and calculate physiological parameters. These outputs may be displayed (126) to a caregiver to indicate the patient's status. The parameters and waveform are obtained at a desired level of accuracy from the sporadic data samples. By pulsing light at sporadic intervals, with an overall reduced sampling frequency, the system may reduce the overall power consumption of the sensor. The sensor operates to emit and detect light and provide detected light data to a processor, without operating at the full data sampling rate of conventional sensors. The reduction in light emission and data sampling can provide savings in power consumption, such that the wireless sensor can operate with a smaller battery and/or for a longer period of time between battery replacement or recharge. In an embodiment, the power consumed by the sporadic sampling is less than or about one quarter ($\frac{1}{4}$) of the power consumed by dense sampling. For example, dense sampling may consume power on the order of about 45 mW, and according to an embodiment, sparse sampling may consume about 10 mW or less. In various embodiments the fraction of power consumed may vary, such as less than or about one half ($\frac{1}{2}$), less than or about one third ($\frac{1}{3}$), less than or about one quarter ($\frac{1}{4}$), less than or about one fifth ($\frac{1}{5}$), or other fractions of the power consumed by dense sampling. The reconstructed waveform and/or calculated physiological parameters may be monitored for quality as described above with reference to FIG. 5.

The set of sporadic data samples includes data samples taken at irregular, non-uniform intervals, such as random or pseudo-random intervals. The average sampling interval of these sporadic samples is longer than the interval used for the fully sampled waveform (i.e., the frequency of the sporadic samples is lower). In one embodiment, a fully sampled waveform includes a dense, uniform set of samples from the waveform at a frequency more than double the Nyquist frequency of the waveform (that is, the frequency identified by the Nyquist-Shannon sampling theorem). In an embodiment, a sporadically sampled waveform includes a sporadic, non-uniform set of samples from the waveform at an average frequency which is also more than double the Nyquist frequency of the waveform, but less than the sampling frequency of a fully-sampled waveform. In an embodiment, a sporadically sampled waveform includes a sporadic, non-uniform set of samples from the waveform at an average frequency less than the Nyquist frequency of the physiological signal, and in another embodiment less than twice the Nyquist frequency. In an embodiment, the sporadically sampled waveform includes a fraction of the number of samples in the fully sampled waveform, such as less than half ($\frac{1}{2}$), one-third ($\frac{1}{3}$), one-fourth ($\frac{1}{4}$), or one-fifth ($\frac{1}{5}$) as many samples. That is, as an example, the sporadically sampled waveform may sample less than or about one half, less than or about one third, less than or about one quarter, less than or about one fifth, or other fractions of the number of samples of the fully sampled waveform. In an embodiment, the sporadically sampled waveform includes an average sampling frequency that is less than or about one half, less than or about one third, less than or about one quarter, less than or about one fifth, or other fractions of a fully sampled frequency of the physiological signal.

The minimum frequency (and maximum duration) for the sampling is determined based on the clinical requirements for the particular waveform and the desired quality or accuracy of the physiological parameter. The reconstructed waveform (reconstructed from the sporadic data samples) is represented by a larger number of samples than are included in the sporadic sample set, resulting in power savings in data acquisition and transmission. In an embodiment, a system includes a dictionary W, a sporadic sample set Y of M samples, and a reconstructed waveform X of N samples, where M<<N. If X is k-sparse, meaning X has at the most k nonzero coefficients in W basis, to be able to reconstruct X from Y, M≥2*k.

The method illustrated in FIG. 7 uses a dictionary of suitable atoms or functions and an iterative process to reconstruct a waveform from a weighted sum of selected functions. In another embodiment, a waveform may be reconstructed from sporadic data samples by using a shift and/or scale approach. In this approach, a first waveform is used as a baseline to reconstruct a second waveform from a sporadic dataset. The first waveform is shifted and/or scaled by calculated coefficients to match the sporadic data samples. The resulting shifted and/or scaled waveform is used as the reconstructed waveform for the sporadic samples. This approach is useful in situations involving two channels of data, such as, for example, light data detected from a pulse oximeter which pulses light at two different wavelengths (such as red and infrared), or electric signals from an EEG (electroencephalography) with 2 or more electrodes. A first waveform is obtained for the first data channel, such as by fully sampling the data channel, or by reconstructing it with the matching pursuit method described above (see FIG. 7). A second waveform for the second data channel can then be obtained by shifting and/or scaling the first waveform.

Figure 8:
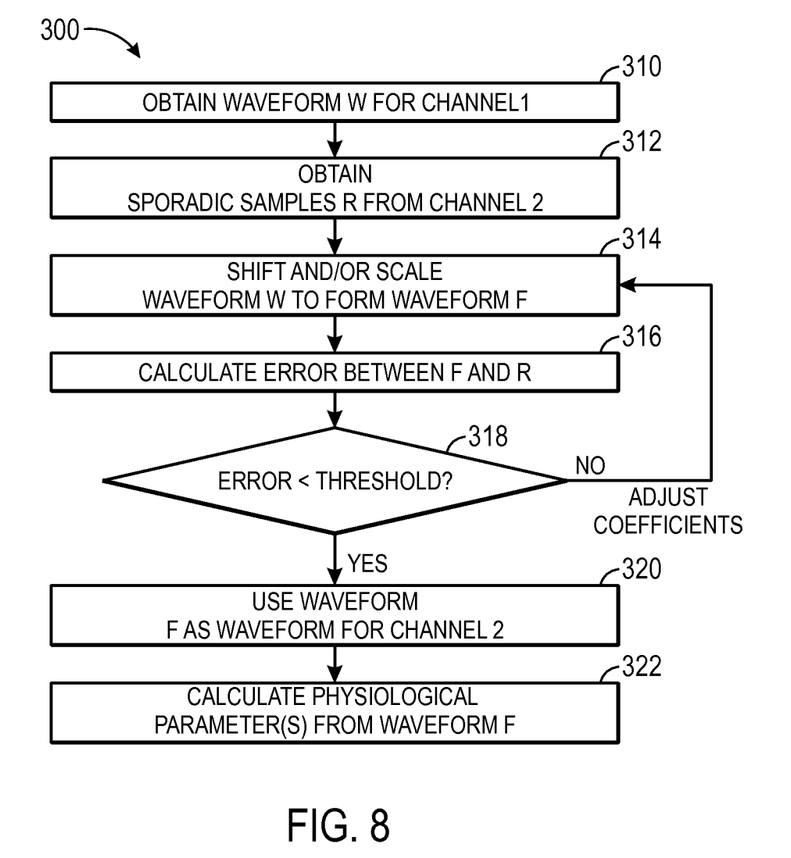
FIG. 8 depicts a flow diagram of a method for obtaining an estimated physiological parameter from the wireless medical system of FIG. 1, in accordance with an embodiment of the present disclosure.

A method 300 for reconstructing a waveform according to another embodiment is illustrated in FIG. 8. The method includes obtaining a first waveform W for a first channel of data (310) over a time period t. The first waveform W may be obtained by iteratively reconstructing the waveform from sporadic data as described with reference to FIG. 7. Alternatively, the first waveform may be obtained by fully sampling the data and interpolating the fully sampled dataset to obtain a waveform.

The method also includes obtaining sporadic samples (S) from a second data channel (312). The sporadic samples may be obtained as described elsewhere herein. The sporadic samples are obtained over a time period that falls within the time duration t of the first waveform. The method includes shifting and/or scaling the first waveform W to create a new waveform X that matches the samples S (314). In an embodiment, the new waveform $X_i$ is calculated as follows: $X_i = a*W(\text{round}(b*i+c))$, where a, b, and c are constant coefficients.

The method then calculates an error by subtracting the samples S from the new waveform $X_i$ (316). The method then compare this error to a threshold (318), and if the error is above a threshold value, then the method adjusts the shifting and/or scaling coefficients a, b, and c and applies them to shift and/or scale the function X (314). This process iteratively repeats until the error is below the threshold. Once the threshold is satisfied, the resulting shifted and/or scaled function X is used as the reconstructed waveform for the second data channel (320). The method may include calculating physiological parameters (322) from the first and/or second waveforms. Different combinations of the matching pursuit and the shifting/scaling approach may be used to reconstruct waveforms for the applicable data channels.

According to an embodiment, a system may be used on a patient to obtain sporadic data samples and provide physiological parameters and/or a waveform for display to a caregiver. It may be desired for the system to frequently update the parameters and/or the waveform in order to show real-time changes in the patient's condition. The system can update the waveform and/or physiological parameters by taking new sporadic samples and generating a new waveform. Obtaining a large number of new samples may provide a suitable resolution for reconstructing a new waveform, but may delay the ultimate display of results to the caregiver. Obtaining a small number of new samples may enable quicker processing, but may not provide sufficient resolution for a new reconstructed waveform. Accordingly, a method is provided for updating a waveform by utilizing new and old samples to provide a timely update of a new waveform with a suitable data resolution.

Figure 9:
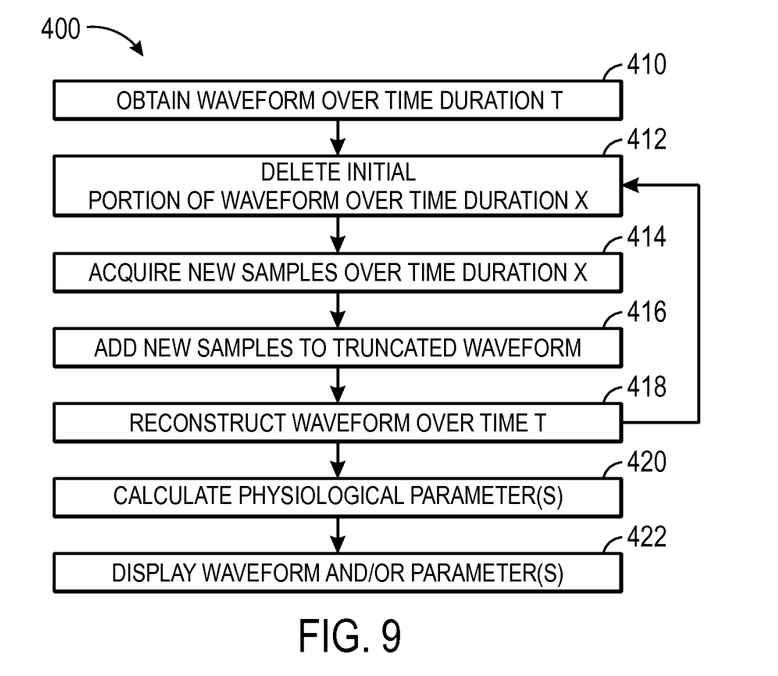
FIG. 9 depicts a flow diagram of a method for updating a calculation of a physiological parameter, according to an embodiment of the present disclosure.

A method 400 for updating a waveform and/or parameters, according to an embodiment, is illustrated in FIG. 9. The method acquires new samples and updates the waveform at a frequency that is higher than the frequency at which the past samples are removed from the waveform. That is, the fidelity of the waveform is based on a time duration of samples that is longer than the time duration of each update. The method includes obtaining a waveform over a time duration T (410). The waveform may be, for example, a reconstructed or waveform as described in any of the above embodiments. The method includes deleting an initial portion of the waveform (412) over a time duration x (with x<T). The result is a truncated waveform spanning a time period of T−x. The method also includes acquiring new sporadic data samples from the patient over the time duration x (414). The method includes appending the new data samples to the truncated waveform (416). The result is a set of data samples spanning a time period T, with data samples from the prior truncated waveform occupying the first T−x duration, and the new sporadic data samples occupying the final x duration. The method includes reconstructing the waveform based on these samples, over the total time duration T (418). This reconstructed waveform overlaps the previous waveform over the period T−x, and includes new samples over the new duration x. The method may include calculating parameters from this new reconstructed waveform (420), and displaying the waveform and/or parameters (422).

When the new waveform is reconstructed, the method returns to truncate this new waveform by removing the oldest portion of the waveform over period x, and combining the truncated waveform with new samples. This process may continue so that the system can continually update the calculated waveform and parameters with newly acquired patient data. The waveform and the calculated parameters are based on data over a time period T, but the updates are provided more quickly, over a shorter time duration x. That is, each x period, a new waveform is reconstructed using the most recent samples over that period x. However, the waveform is reconstructed based on data covering the larger time period T, providing a larger resolution/fidelity for calculation of the waveform and the patient parameters.

Although various embodiments of a medical system and method have been disclosed herein, many modifications and variations will be apparent to those skilled in the art. It is to be understood that embodiments according to the present disclosure may be embodied other than as specifically described herein. The invention is also defined in the following claims.

What is claimed is:

1. A system comprising:
light drive circuitry configured to drive an emitter of a pulse oximetry sensor at an average frequency and an average pulse width to cause the emitter to emit light into a tissue of the patient at the average frequency and the average pulse width;
a processor configured to:
receive a set of data samples generated by a detector of the pulse oximetry sensor based on the light that passed through the tissue of the patient, wherein the set of data samples are indicative of a physiological signal of the patient, and the average frequency and the average pulse width cause the set of data samples to comprise an average sampling frequency less than twice the Nyquist frequency of the physiological signal;
construct a waveform representative of the physiological signal based on the set of data samples; and
calculate a physiological parameter based on the waveform.

2. The system of claim 1, comprising the pulse oximetry sensor, wherein the pulse oximetry sensor and the processor are coupled wirelessly.

3. The system of claim 1, further comprising a display coupled to the processor configured to display the waveform and/or the physiological parameter.

4. The system of claim 3, wherein the display is configured to display a portion of the waveform spanning a first time duration, and wherein the processor is configured to update the waveform based on an updated set of data samples spanning a second time duration shorter than the first time duration.

5. The system of claim 1, wherein the set of data samples comprise an average sampling frequency less than the Nyquist frequency of the physiological signal.

6. The system of claim 1, wherein the set of data samples comprise an average sampling frequency less than a fully sampled frequency of the physiological signal.

7. The system of claim 1, wherein the set of data samples comprise an average sampling frequency less than one quarter of a fully sampled frequency of the physiological signal.

8. The system of claim 1, wherein the processor is configured to construct the waveform by matching pursuit.

9. The system of claim 8, wherein the processor is configured to access a dictionary of components.

10. The system of claim 9, wherein the dictionary is customized based on the physiological signal.

11. The system of claim 1, comprising the pulse oximetry sensor, the emitter, and the detector, wherein the emitter comprises a first light emitting diode (LED) configured to emit red light and a second LED configured to emit infrared light, the detector is configured to generate the set of data samples corresponding to the red light and a second set of data samples corresponding to the infrared light, the processor is configured to construct the waveform by matching pursuit based on the set of data samples, and the processor is configured to construct a second waveform by shifting and/or scaling the waveform based on the second set of data samples.

12. The system of claim 11, wherein the processor is configured to calculate the physiological parameter based on the waveform and the second waveform.

13. The system of claim 12, wherein the physiological parameter is blood oxygenation.

14. The system of claim 1, comprising the pulse oximetry sensor, the emitter, and the detector.

15. The system of claim 1, wherein the processor is configured to:
select a function from a dictionary based on the set of data samples;
iteratively calculate a residual and an approximation based on the selected function; and
construct the waveform based on the approximation.

16. The system of claim 1, wherein the light drive circuitry is configured to drive the emitter at irregular intervals to cause the emitter to emit light into the tissue of the patient at irregular intervals comprising the average frequency and the average pulse width.

17. A method comprising:
emitting light sporadically over a period of time into a tissue of a patient via an emitter of a pulse oximetry sensor at a first average frequency corresponding to an average sampling frequency;
generating, via a detector of the pulse oximetry sensor, a set of sporadic data samples over the period of time and indicative of a physiological signal of the patient based on the light that passed through the tissue of the patient;
receiving the set of sporadic data samples at a processor;
using the processor to construct a waveform corresponding to the physiological signal based on the set of sporadic data samples; and
calculating a physiological parameter based on the waveform.

18. The method of claim 17, wherein constructing the waveform comprises:
selecting from a dictionary a component, based on the set of sporadic data samples;
calculating a waveform approximation and a residual based on the selected dictionary component; and
repeating the selection until the residual falls below a threshold.

19. The method of claim 18, further comprising orthogonalizing the selected dictionary component.

20. The method of claim 18, wherein selecting the component comprises finding a function with the largest dot product between the function and the residual.

21. The method of claim 18, further comprising
generating, via the detector of the pulse oximetry sensor, a second set of sporadic data samples over the period of time and indicative of the physiological signal of the patient based on the light that passed through the tissue of the patient; and
using the processor to construct a second waveform by shifting and/or scaling the waveform based on the second set of sporadic data samples.

22. The method of claim 21, comprising, using the processor, calculating the physiological parameter based on the waveform and the second waveform.

23. The method of claim 22, wherein the physiological parameter is blood oxygenation.

24. The method of claim 17, further comprising obtaining a first waveform, and wherein constructing the waveform comprises shifting and/or scaling the first waveform.

25. The method of claim 17, wherein the set of sporadic data samples comprises the average sampling frequency, and wherein the method further comprises calibrating the average sampling frequency.

26. The method of claim 25, wherein calibrating the average sampling frequency comprises:
emitting light at regular intervals over a second period of time into the tissue of the patient via the emitter of the pulse oximetry sensor at a second average frequency greater than the first average frequency;
generating, via the detector of the pulse oximetry sensor, a fully sampled dataset indicative of the physiological signal of the patient based on the light that passed through the tissue of the patient, the fully sampled dataset comprising a respective average sampling frequency of at least twice the Nyquist frequency of the physiological signal;
receiving the fully sampled dataset at the processor;
interpolating the fully sampled dataset to generate a first waveform;
sampling the first waveform at a first average sampling frequency to obtain calibration data samples;
constructing a calibration waveform based on the calibration data samples;
calculating an error between the calibration waveform and the first waveform; and
providing a light drive signal to the emitter to adjust the first average frequency at which the emitter emits light into the tissue of the patient to cause the detector to generate the set of sporadic data samples comprising the average sampling frequency based on the error.

27. The method of claim 25, wherein the calibrating is triggered based on a signal quality indication or a timer.

28. The method of claim 17, further comprising displaying the waveform or the physiological parameter.

29. The method of claim 17, further comprising displaying the waveform over a first time duration and updating the displayed waveform, wherein updating comprises obtaining a new set of sporadic data samples over a second time duration shorter than the first time duration, removing an initial portion of the displayed waveform that spans the second time duration to form a truncated waveform, adding the new set of sporadic data samples to the truncated waveform, generating a new waveform based on the new set of sporadic data samples and the truncated waveform, and displaying the new waveform.

30. A method comprising:
emitting light pulses into a tissue of a patient via an emitter of a pulse oximetry sensor at an average frequency and an average pulse width over a period of time;
generating, via a detector of the pulse oximetry sensor, a set of data samples indicative of a physiological signal of the patient based on the light pulses that passed through the tissue of the patient, wherein the average frequency and the average pulse width cause the detector to generate the set of data samples comprising an average sampling frequency less than twice the Nyquist frequency of the physiological signal over the period of time;

wirelessly transmitting the set of data samples from the pulse oximetry sensor to a processor;

selecting, using the processor, a function based on the set of data samples;

iteratively calculating a residual and an approximation based on the selected function;

generating a waveform, based on the approximation, that corresponds to the physiological signal; and calculating, using the processor, a physiological parameter based on the waveform.

31. The method of claim 30, wherein the average frequency is between approximately 100 to 700 milliseconds and the average pulse width is between approximately 10 to 50 milliseconds.

32. The method of claim 30, comprising emitting the light pulses at irregular intervals over the period of time, thereby causing the set of data samples to include data samples spread at irregular intervals over the period of time.

* * * * *